United States Patent
Russo et al.

(10) Patent No.: US 7,026,509 B2
(45) Date of Patent: Apr. 11, 2006

(54) CYCLIC PHOSPHAZENE COMPOUNDS AND USE THEREOF AS ADDITIVES OF PERFLUOROPOLYETHER OILS

(75) Inventors: Antonio Russo, Milan (IT); Patrizia Maccone, Milan (IT); Claudio Tonelli, Milan (IT)

(73) Assignee: Solvay Solexis S.p.A., Milan (IT)

( * ) Notice: Subject to any disclaimer, the term of this patent is extended or adjusted under 35 U.S.C. 154(b) by 195 days.

(21) Appl. No.: 10/366,414

(22) Filed: Feb. 14, 2003

(65) Prior Publication Data

US 2003/0176738 A1 Sep. 18, 2003

(30) Foreign Application Priority Data

Feb. 14, 2002 (IT) .................... MI2002A0281

(51) Int. Cl.
*C10M 107/38* (2006.01)
*C09K 15/32* (2006.01)
*C07K 9/547* (2006.01)

(52) U.S. Cl. .................... 564/13; 508/422; 508/582; 252/400.23

(58) Field of Classification Search .............. 508/442, 508/582; 252/400.23; 564/13; 548/100, 262.2, 548/259.4; 514/359, 83
See application file for complete search history.

(56) References Cited

U.S. PATENT DOCUMENTS

| | | | |
|---|---|---|---|
| 3,201,455 A | 8/1965 | Russell et al. | 260/475 |
| 3,214,478 A | 10/1965 | Milian et al. | 260/615 |
| 3,665,041 A | 5/1972 | Sianesei et al. | 260/615 A |
| 3,715,378 A | 2/1973 | Slanesi et al. | 260/465 |
| 4,523,039 A | 6/1985 | Lagow et al. | 568/615 |
| 5,124,058 A | 6/1992 | Corti et al. | 252/54 |

FOREIGN PATENT DOCUMENTS

| | | |
|---|---|---|
| EP | 0 148 482 | 7/1985 |
| EP | 0287892 A2 | 10/1988 |
| EP | 0435062 A1 | 7/1991 |
| EP | 1219629 A1 | 7/1992 |
| EP | 0597369 A1 | 5/1994 |
| GB | 1 226 566 | 3/1971 |
| WO | WO 87/00538 | 1/1987 |

OTHER PUBLICATIONS

CA:135:180769 abs of WO 2001058880 Aug. 2001.*

* cited by examiner

*Primary Examiner*—Peter O'Sullivan
(74) *Attorney, Agent, or Firm*—Arent Fox PLLC

(57) ABSTRACT

Cyclic phosphazene compounds of formula (I):

$$\left( \begin{array}{c}(AR'_fCF_2CH_2O)_\beta \\ (HOCH_2R_fCH_2O)_\alpha\end{array} \right) Q \left( \begin{array}{c}(AR'_fCF_2CH_2O)_\varepsilon \\ OCH_2R_fCH_2O-Q\end{array} \right)_\omega$$

$$-(OCH_2R_fCH_2O)_\gamma - Q \begin{array}{c}(OCH_2CF_2R'_fA)_\beta \\ (OCH_2R_fCH_2OH)_\alpha\end{array}$$

wherein:

Q is a cyclic compound of formula:

A is an end group of the —OCF$_2$X, —OC$_2$F$_4$X, —OC$_3$F$_6$X type, wherein X=F, Cl, H;

R$_f$ and R'$_f$ are (per)fluoropolyoxyalkylene chains having a number average molecular weight in the range 280–5,000.

19 Claims, No Drawings

CYCLIC PHOSPHAZENE COMPOUNDS AND USE THEREOF AS ADDITIVES OF PERFLUOROPOLYETHER OILS

The present invention relates to anti-wear additives for lubricating oils and greases.

More specifically the invention relates to additives having improved anti-wear properties combined with improved solubility in perfluoropolyether oils, to the process for their preparation and to compositions of oils or greases, preferably having a perfluoropolyether structure comprising said additives.

It is known that lubricants are largely used in systems containing moving mechanical parts, and in contact with each other, mainly to reduce the wear of said mechanical parts. Said lubricants to have good anti-wear properties in the time must be formulated with additives. Said additives must be soluble in the lubricant to guarantee the constancy and the uniformity of their anti-wear performances.

It is also known in the prior art that perfluoropolyethers have a very good chemical, thermal and oxidative stability such to allow the use thereof as oils, greases or hydraulic fluids in many applications where hydrogenated or silicone based oils or greases are not suitable. Among said lubricants having a perfluoropolyether structure available on the market, FOMBLIN® sold by Ausimont S.p.A. can be mentioned.

The anti-wear properties of the perfluoropolyether lubricants and those of the mineral oils do not satisfy the anti-wear properties required in many applications. Therefore said lubricants require the use of anti-wear additives.

The anti-wear additives used in conventional lubricants, such for example mineral or silicone oils, are not suitable to be used in perfluorinated lubricants due to their insolubility in the latter.

In U.S. Pat. No. 5,124,058 perfluoropolyether oils containing anti-wear additives are described, having the following perfluoropolyether structure of general formula $$TO(CF_2O)_m(CF_2CF_2O)_n(CF_2CF(CF_3)O)_s(CF(CF_3)O)_pT'$$

wherein:

T,T' are equal or different from each other and selected from —CF$_2$X, —C$_2$F$_4$X, —C$_3$F$_6$X with X=F, Cl or fluorinated end groups containing reactive groups as carboxyls, ketones, amides, amines, alkoxyls, with the proviso that at least one of the two end groups contains one of said reactive groups; m, n, s, p are integers such that the average molecular weight is in the range 1,000–100,000. The additive concentrations in the perfluoropolyether lubricant are comprised between 0.5% and 10%. However to obtain wear values of 0.56 mm, determined by the ASTM D 4172B method, additive concentrations higher than or equal to 3% by weight must be used. For example if a Fomblin® perfluoropolyether oil having viscosity equal to 1,850 cSt at 20° C. is used, to obtain a 50% wear decrease, 5% amounts of said additive must be used.

The need was therefore felt to have available additives usable at lower concentrations, and giving improved anti-wear properties, compared with the antiwear products of the prior art.

The Applicant has surprisingly and unexpectedly found additives capable to satisfy the above combination of properties.

An object of the present invention are cyclic phosphazene compounds of general formula (I):

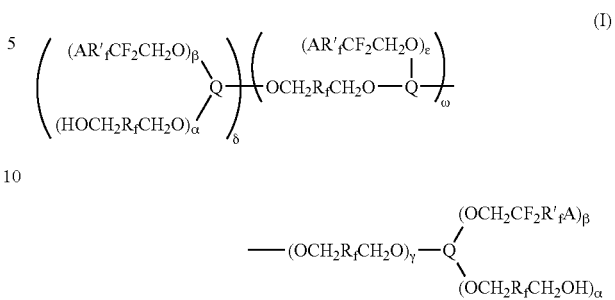

wherein:

Q is a cyclic phosphazene structure

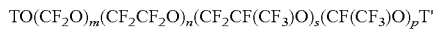

wherein n' is an integer equal to 3 or 4, ω=0 or 1, preferably 0, ε=4 or 6, γ=0 or 1, α and β are integers from 0 to 8, δ=0 or 1, with the proviso that:

when n'=3 and γ=1 then ε=4, α and β are integers from 0 to 5, such that (α+β) is equal to 5; δ=1;

when n'=3 and γ=0 then ε=4, α and β are integers from 0 to 6, such that (α+β) is equal to 6, ω and δ are equal to 0;

when n'=4 and γ=1 then ε is equal to 6, α and β are integers from 0 to 7, such that (α+β) must be equal to 7 and δ=1;

when n'=4 and γ=0 then ε is equal to 6, α and β are integers from 0 to 8, such that (α+β) must be equal to 8, ω and δ are equal to 0;

A is an end group of the —OCF$_2$X, —OC$_2$F$_4$X, —OC$_3$F$_6$X type, wherein X=F, Cl, H;

R$_f$ and R'$_f$ are (per)fluoropolyoxyalkylene chains having a number average molecular weight in the range 280–5,000, preferably 500–2,000 and comprising one or more repeating units statistically distributed along the chain selected from (C$_3$F$_6$O); (CFYO) wherein Y is F or CF$_3$; (C$_2$F$_4$O); (CF$_2$(CF$_2$)$_{x'}$CF$_2$O) wherein x' is an integer equal to 1 or 2; (CR$_4$R$_5$CF$_2$CF$_2$O) wherein R$_4$ and R$_5$ are equal to or different the one from the other and selected between H, Cl and wherein one fluorine atom of the perfluoromethylene unit can optionally be substituted with H, Cl or (per)fluoroalkyl, preferably having from 1 to 4 carbon atoms.

The invention phosphazenes satisfy the following test: they are completely soluble, up to at least concentrations of 10% by weight, in FOMBLIN® Y25 perfluoropolyether oil having viscosity 250 cSt at 20° C. and a structure

wherein:

B=B'=C$_3$F$_7$ and X=CF$_3$; m' and n' are integers such that the viscosity has the above value.

With solubility of the invention compound in FOMB-LIN® Y25 it is meant that the mixture is clear and there is no opalescence, turbidity or phase separation after mixture stirring.

In particular the preferred compounds according to the invention are the following:

$$(N=P)_{n'}\begin{matrix}OCH_2CF_2R'_fA\\|\\|\\OCH_2CF_2R'_fA\end{matrix} \quad (II)$$

$$(AR'_fCH_2CH_2O)_\beta\underset{(HOCH_2R_fCH_2O)_\alpha}{\overset{}{\underset{}{P}}}\begin{matrix}N\\\|\\N\end{matrix}\underset{}{P}\left(\begin{matrix}AR'_fCF_2CH_2O & OCH_2CF_2R'_fA\\ \underset{}{P}\\ N & N\\ \|\ & \|\\ P & P\\ AR'_fCF_2CH_2O & OCH_2CF_2R'_fA\end{matrix}\right)_\omega -OCH_2R_fCH_2O-\underset{}{P}\begin{matrix}(OCH_2CF_2R'_fA)_\beta\\ N\\\|\\ N\\ (OCH_2R_fCH_2OH)_\alpha\end{matrix} \quad (III)$$

wherein:
n' is an integer equal to 3 or 4;
A is an end group of the —$OCF_2X$, —$OC_2F_4X$, —$OC_3F_6X$ type, wherein X=F, Cl, H;
ω is an integer equal to 0 or 1, preferably 0;
α and β are integers comprised between 0 and 5, such that α+β must be equal to 5;
$R_f$ and $R'_f$ are as above.

The preferred $R_f$ are the following perfluoropolyoxyalkylene units statistically distributed along the chain:

$$-CF_2-O-(CF_2CF_2O)_{p'}(CF_2O)_{q'}-CF_2- \quad (a)$$

wherein:
p' and q' are numbers such that the q'/p' ratio is comprised between 0.2 and 2 and the number average molecular weight is in the above range;

$$-CFY-O-(CF_2CF(CF_3)O)_{r'}-(CF_2CF_2O)_{s'}-(CFYO)_{t'}-CFY-$$

wherein:
Y is as above; r', s' and t' are numbers such that r'+s' is in the range 1–50, the t'/(r'+s') ratio is comprised between 0.01 and 0.05, and the molecular weight is in the above range;

$$-CF(CF_3)(OCFY)_{t'}(OC_3F_6)_{u'}-OR''_fO-\\(C_3F_6O)_{u'}(CFYO)_{t'}CF(CF_3)- \quad (c)$$

wherein:
$R''_f$ is a $C_1$–$C_8$ perfluoroalkylene; u'+t' is a number such that the number average molecular weight is in the above range; t' can have also the value of zero; Y is as above;

$$-CF_2CF_2O-(CF_2(CF_2)_{x'}CF_2O)_{v'}-CF_2CF_2- \quad (d)$$

wherein:
v' is a number such that the molecular weight is in the above range and x' is 1 or 2;

$$-CF_2CH_2-(OCF_2CF_2CH_2)_{w'}-OR''_fO-(CH_2CF_2CF_2O)_{w'}-\\CH_2CF_2- \quad (e)$$

wherein:
$R''_f$ is as above; w' is a number such that the number average molecular weight is in the above range.

The preferred $R'_f$ are the following perfluoropolyoxyalkylene units statistically distributed along the chain:

$$-(C_3F_6O)_q(CFYO)_r- \quad (a')$$

wherein Y is —F, —$CF_3$; q and r are integers, the q/r ratio is ≧2;

$$-(C_3F_6O)_q- \quad (b')$$

wherein q is an integer, wherein the number average molecular weight is that above;

$$-(C_3F_6O)_q(C_2F_4O)_t(CFYO)_r- \quad (c')$$

wherein Y is —F, —$CF_3$; q, t and r are integers such that the number average molecular weight is that above.

The preferred formula (II) phosphazenes are those having n'=3, i.e. of general formula (IIA)

$$\begin{matrix}N\overset{P}{\underset{\|}{\diagup}}N\\|\quad\quad\|-[OCH_2CF_2R'_fA]_6\\P\underset{N}{\diagdown}P\end{matrix} \quad (IIA)$$

wherein $R'_f$ has structure (a') and a number average molecular weight between 500 and 700, Y=—$CF_3$ and A=—$OC_3F_6Cl$.

Also formula (IIB) compounds can be used, wherein the phosphazene ring has 4 —N=P— groups.

$$\begin{matrix}N=P\\\diagup\quad\diagdown\\P\quad\quad N\\\|\quad\quad\|-[OCH_2CF_2R'_fA]_8\\N\quad\quad P\\\diagdown\quad\diagup\\P=N\end{matrix} \quad (IIB)$$

The preferred formula (III) phosphazenes are those with ω and α equal to 0 having general formula (IIIA):

$$(AR'_fCF_2CH_2O)_5\underset{P\diagdown N\diagup P}{\overset{N\diagup P\diagdown N}{\|\quad\|}}-OCH_2R_fCH_2O-\underset{P\diagdown N\diagup P}{\overset{N\diagup P\diagdown N}{\|\quad\|}}(OCH_2CF_2R'_fA)_5 \quad (IIIA)$$

wherein $R'_f$ has structure (a') and number average molecular weight in the range 500–700, Y=—$CF_3$ and A=—$OC_3F_6Cl$; $R_f$ has structure (a) and a number average molecular weight in the range 1,000–2,000.

The Applicant has surprisingly and unexpectedly found that the invention compounds can be used as additives of perfluorinated lubricants, such for example perfluoropolyether based oils or greases, giving anti-wear performances higher than those obtained with known additives, such for example those described in U.S. Pat. No. 5,124,058, in terms of absolute wear values and the used lower concentrations. Besides, the invention compounds are soluble in perfluoropolyether oils as above defined.

The phosphazenes object of the invention are viscous, transparent and odourless liquids.

A further object of the present invention are compositions having lubricating anti-wear properties comprising:

an oil or a grease having a perfluoropolyether structure;
from 0.05 to 10% by weight, preferably from 0.4 to 5% by weight, of one or more phosphazenes of the present invention.

The phosphazenes, at the above concentrations, are, as said, completely soluble in the lubricants having a perfluoropolyoxyalkylene structure, and the composition maintains unchanged the high oil or grease thermal and chemical stability. The perfluoropolyethers usable in the oil and grease preparation are available on the market such for example FOMBLIN®, Krytox®, Demnum®.

As examples of perfluoropolyether oils the following classes can be mentioned:

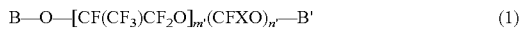  (1)

wherein
X is equal to —F or —$CF_3$,
B and B', equal to or differnt from each other, are selected from —$CF_3$, —$C_2F_5$ or —$C_3F_7$;
m' and n' are integers such that the m'/n' ratio is comprised between 20 and 1,000 and the product viscosity is between 10 and 4,000 cSt; the various units are statistically distributed along the chain.

Said products can be obtained by photooxidation of the perfluoro propene as described in GB 1,104,432, and by subsequent conversion of the end groups as described in GB 1,226,566.

$C_3F_7O$—[$CF(CF_3)CF_2O$]$_{o'}$-D  (2)

wherein
D is equal to —$C_2F_5$ or —$C_3F_7$;
o' is an integer such that the product viscosity is in the above range.

Said products can be prepared by ionic perfluoropropylenoxide oligomerization and subsequent treatment with fluorine as described in U.S. Pat. No. 3,242,218.

{$C_3F_7O$—[$CF(CF_3)CF_2O$]$_{p'}$—$CF(CF_3)$—}$_2$  (3)

wherein
p' is an integer such that the product viscosity is in the above range.

Said products can be obtained by ionic telomerization of the perfluoropropylenoxide and subsequent photochemical dimerization as reported in U.S. Pat. No. 3,214,478.

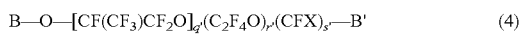  (4)

wherein
X is equal to —F or —$CF_3$;
B and B', equal to or different from each other, are selected from —$CF_3$, —$C_2F_5$ or —$C_3F_7$;
q', r' and s' are integers, the 0 also comprised, such that the product viscosity is in the above range.

Said products are obtainable by photooxidation of a mixture of $C_3F_6$ and $C_2F_4$ and subsequent treatment with fluorine as described in U.S. Pat. No. 3,665,041.

B—O—($C_2F_4O$)$_{t'}$($CF_2O$)$_{u'}$—B'  (5)

wherein
B and B', equal to or different from each other, are selected from —$CF_3$, —$C_2F_5$ or —$C_3F_7$;
t' and u' are integers such that the t'/u' ratio is comprised between 0.1 and 5 and the product viscosity is in the above range.

Said products are obtained by photooxidation of $C_2F_4$ as reported in U.S. Pat. No. 3,715,378 and subsequent treatment with fluorine as described in U.S. Pat. No. 3,665,041.

B—O—($CF_2CF_2CF_2O$)$_{v'}$—B'  (6)

wherein
B and B', equal to or different from each other, are selected from —$CF_3$, —$C_2F_5$ or —$C_3F_7$;
v' is an integer such that the product viscosity is in the above range.

Said products are obtained as reported in EP 148,482.

D—O—($CF_2CF_2O$)$_{z'}$-D'  (7)

wherein
D and D', equal to or different from each other, are selected from —$C_2F_5$ or —$C_3F_7$;
z' is an integer such that the product viscosity is in the above range.

Said products can be obtained as reported in U.S. Pat. No. 4,523,039.

$R'''_f$—[$C(CF_3)_2$—O—$C(R''_f)_2C(R''_f)_2$—O]$_{w'}$—$R'''_f$  (8)

wherein
$R'''_f$ is a perfluoroalkyl group;
$R''_f$ is equal to —F or perfluoroalkyl;
w' represents a number higher than or equal to 8.

Said products can be obtained as reported in patent application WO 87/00,538.

The preferred perfluoropolyether oils are those of the classes (1), (2), (4), (5) and (6). The perfluoropolyethers of the above classes from (1) to (8), have perfluoroalkyl end groups, are liquid with a very low vapour tension value and have a viscosity, at 20° C., generally comprised between 50 and 100,000 cSt, preferably between 100 and 2,000 cSt.

The invention formulations can also contain other additives commonly used in formulations of perfluoropolyether lubricants such as for example anti-rust or antioxidant additives.

A further object of the present invention is a process to prepare the invention phosphazenes by reaction, in the presence of a base, of a perchlorophosphazene of formula (IV) or (V):

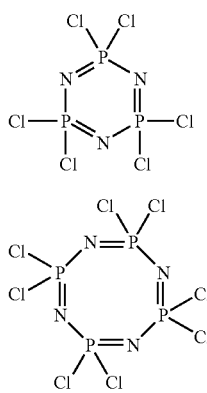

(IV)

(V)

with a fluorinated alcohol of formula AR'$_f$CF$_2$CH$_2$OH or optionally in admixture with an alcohol of formula HOCH$_2$R$_f$CH$_2$OH, wherein A and R$_f$, R'$_f$ have the above meaning.

More specifically the process to obtain the phosphazenes of the invention comprises the following steps:

(A) Condensation reaction between a fluorinated alcohol of formula AR'$_f$CF$_2$CH$_2$OH, or a mixture thereof with an alcohol of formula HOCH$_2$R$_f$CH$_2$OH, with the perchloro phosphazene of formula (IV) or (V), in an equivalent ratio alcohol/phosphazenes 1:1. Said reaction is carried out in one step, in an organic solvent, in the presence of a base and of a phase transfer agent, at a temperature in the range 20° C.–100° C., preferably 40° C.–80° C. The organic solvent is selected from the known fluorinated or hydrofluorinated solvents of the prior art and having a boiling point in the range 20° C.–150° C., preferably 40° C.–100° C., maintaining a ratio by weight solvent/fluorinated alcohol in the range 0.5–10, preferably 2–5. As a base it is used an aqueous solution of NaOH or KOH at a concentration comprised between 20% and 60% w/w, preferably between 30% and 50% w/w, in amounts to have a KOH or NaOH excess comprised between 2 and 10 times the fluorinated alcohol. The phase transfer agent is preferably a phosphonium salt or a quaternary ammonium salt known in the prior art, for example tetrabutylammonium hydroxide, tetramethylammonium chloride, used in a molar concentration comprised between 1% and 10% the fluorinated alcohol. Depending on the temperature there are reaction times generally comprised between 8 and 24 hours. At the reaction end the phases are allowed to separate and the heavy organic phase is recovered.

(B) The heavy organic phase obtained in step (A) is repeatedly washed with water to remove the phase transfer agent and the inorganic salts generated during the reaction. The obtained product is then separated from the solvent by known methods, for example by evaporation. The phosphazenes have been isolated with a yield higher than 90%.

When in step A) both monofunctional AR'$_f$CF$_2$CH$_2$OH and bifunctional HOCH$_2$R$_f$CH$_2$OH fluorinated alcohols are used, they are preferably added, separately, to the perchloro phosphazene, in more steps, in the following order: first the monofunctional alcohol is added to convert the 50% of the phosphazene chlorine atoms, then the bifunctional alcohol is added to let react on an average no more than one chlorine atom for phosphazene ring, lastly the remaining chlorine atoms are let completely react with a further addition of the monofunctional alcohol.

The present invention will be better illustrated by the following Examples, which have a merely illustrative but not limitative purpose of the invention.

EXAMPLES

Preparation of the Compounds

Example 1

Preparation of the Formula (IIA) Compound wherein A=a Molar Mixture 60/40 of ClCF$_2$—CF (CF$_3$)—O— and CF$_3$—CFCl—CF$_2$—O— and R'$_f$=(CF(CF$_3$)—CF$_2$—O—)$_m$ with m=1–4 Such that AR'$_f$CF$_2$CH$_2$O— has a Number Average Molecular Weight Equal to 593

150 g (0.252 eq) of AR'$_f$CF$_2$CH$_2$OH (MW=594) of above defined formula, 4.9 g of an aqueous solution at 40% by weight of Et$_4$N$^+$OH$^-$, 380 g of a mixture of perfluorobutyltetrahydrofuran and perfluoropropyl tetrahydropyran as solvent, 14.6 g (0.042 moles) of hexachlorocyclotriphosphazene and 235 g of an aqueous solution of KOH at 30% by weight are introduced in a 1 liter glass reactor equipped with mechanical stirrer, thermometer and a reflux condenser. The reaction mixture is heated at 60° C. and kept under stirring for about 15 hours. After cooling the phases are allowed to separate and the heavy organic phase is separated and washed with 150 g of water. The organic phase is separated again and washed a second time with 150 g of an aqueous HCl solution at 2% by weight. After the organic phase separation the solvent is distilled and the product stripped at 150° C. at a residual pressure of 10$^{-2}$ mbar for about 4 hours. 144 g of product are thus obtained with a yield equal to 93%. The IR and NMR ($^{31}$P, $^1$H, $^{13}$C and $^{19}$F) analyses confirm the structure of the above indicated product.

Example 2

Preparation of the General Formula (IIA) Derivative wherein A=a 60/40 Mixture of HCF$_2$—CF(CF$_3$)—O— and CF$_3$—CFH—CF$_2$—O— and R'$_f$=(CF(CF$_3$)—CF$_2$—O—)$_m$ with m=1–4 Such that AR'$_f$CF$_2$CH$_2$O— has a Number Average Molecular Weight Equal to 557

150 g (0.269 eq) of AR'$_f$CF$_2$CH$_2$OH (MW=558) of above defined formula, 5.2 g of an aqueous solution at 40% by weight of Et$_4$N$^+$OH$^-$, 380 g of a mixture of perfluorobutyltetrahydrofuran and perfluoropropyl tetrahydropyran as solvent, 15.7 g (0.045 moles) of hexachlorocyclotriphosphazene and 250 g of an aqueous KOH solution at 30% by weight are introduced in a 1 liter glass reactor equipped with mechanical stirrer, thermometer and a reflux condenser. The reaction mixture is heated at 60° C. and kept under stirring for about 15 hours. After cooling the phases are allowed to separate and the heavy organic phase is separated and washed with 150 g of water. The organic phase is separated again and washed a second time with 150 g of an aqueous HCl solution at 2% by weight. After the organic phase separation the solvent is distilled and the product stripped at 150° C. at a residual pressure of 10$^{-2}$ mbar for about 4 hours. 142 g of product are thus obtained with a yield equal to 90.76. The IR and NMR ($^{31}$P, $^1$H, $^{13}$C and $^{19}$F) analyses confirm the product structure.

Example 3

Preparation of the General Formula (IIA) Dervative wherein A=—OCF$_3$, CF$_3$CF$_2$O—, CF$_3$CF$_2$CF$_2$O— and R'$_f$=—(CF(CF$_3$)CF$_2$O)$_o$—(CFXO)$_p$— wherein X is Equal to —F or —CF$_3$; o and p are Numbers Such that the p/o Ratio is in the Range 0.01–0.5, and Such that AR'$_f$CF$_2$CH$_2$O— has a Number Average Molecular Weight Equal to 729

150 g (0.205 eq) of AR'$_f$CF$_2$CH$_2$OH (MW=730) of the above defined formula, 4 g of an aqueous solution at 40% by weight of $Et_4N^+OH^-$, 380 g of a mixture of perfluorobutyltetrahydrofuran and perfluoropropyl tetrahydropyran as solvent, 11.9 g (0.034 moles) of hexachlorocyclotriphosphazene and 200 g of an aqueous KOH solution at 30% by weight are introduced in a 1 liter glass reactor equipped with mechanical stirrer, thermometer and a reflux condenser. The reaction mixture is heated at 60° C. and kept under stirring for about 15 hours. After cooling the phases are allowed to separate and the heavy organic phase is separated and washed with 150 g of water. The organic phase is separated again and washed a second time with 150 g of an aqueous HCl solution at 2% by weight. After the organic phase separation the solvent is distilled and the product stripped at 150° C. at a residual pressure of $10^{-2}$ mbar for about 4 hours. 146 g of product are thus obtained with a yield equal to 95%. The IR and NMR ($^{31}P$, $^1H$, $^{13}C$ and $^{19}F$) analyses confirm the product structure.

Example 4

Preparation of the Formula (IIIA) Derivative wherein A=a 60/40 Mixture of $ClCF_2$—$CF(CF_3)$—O— and $CF_3$—$CFCl$—$CF_2$—O— and $R'_f$=—(CF(CF_3)—$CF_2$—O—$)_m$ with m=1–4 Such that $AR'_fCF_2CH_2O$— has a Number Average Molecular Weight Equal to 593 and —$OCH_2R_fCH_2O$—, wherein $R_f$ has Repeating Units as Defined in (c) in the Text, has an Average Molecular Weight of 487

127.8 g (0.215 moles) of $AR'_fCF_2CH_2OH$ (MW=594) of the above defined formula, 10.27 g (0.021 moles) of $HOCH_2R_fCH_2OH$ (MW=489), 4 g of an aqueous solution at 40% by weight of $Et_4N^+OH^-$, 380 g of a mixture of perfluorobutyltetrahydrofuran and perfluoropropyl tetrahydropyran as solvent, 15 g (0.043 moles) of hexachlorocyclotriphosphazene and 200 g of an aqueous KOH solution at 30% by weight are introduced in a 1 liter glass reactor equipped with mechanical stirrer, thermometer and a reflux condenser. The reaction mixture is heated at 60° C. and kept under stirring for about 15 hours. After cooling the phases are allowed to separate and the heavy organic phase is separated and washed with 150 g of water. The organic phase is separated again and washed a second time with 150 g of an aqueous HCl solution at 2% by weight. After the organic phase separation the solvent is distilled and the product stripped at 150° C. at a residual pressure of $10^{-2}$ mbar for about 4 hours. 134 g of product are thus obtained with a yield equal to 96%. The IR and NMR ($^{31}P$, $^1H$, $^{13}C$ and $^{19}F$) analyses confirm the product structure.

Example 5

Preparation of the Formula (IIIA) Derivative wherein A=a 60/40 Mixture of $ClCF_2$—$CF(CF_3)$—O— and $CF_3$—$CFCl$—$CF_2$—O— and $R'_f$=(CF(CF_3)—$CF_2$—O$)_m$ with m=1–4 Such that $AR'_fCF_2CH_2O$ has a Number Average Molecular Weight Equal to 593 and —$OCH_2R_fCH_2O$—, wherein $R_f$ has Repeating Units as Defined in (a) in the Text, has an Average Molecular Weight of 1437

127.8 g (0.215 moles) of $AR'_fCF_2CH_2OH$ (MW=594) of the above defined formula, 30.9 g (0.021 moles) of $HOCH_2R_fCH_2OH$ (MW=1439), 4 g of an aqueous solution at 40% by weight of $Et_4N^+OH^-$, 380 g of a mixture of perfluorobutyltetrahydrofuran and perfluoropropyl tetrahydropyran as solvent, 15 g (0.043 moles) of hexachlorocyclotriphosphazene and 200 g of an aqueous KOH solution at 30% by weight are introduced in a 1 liter glass reactor equipped with mechanical stirrer, thermometer and a reflux condenser. The reaction mixture is heated at 60° C. and kept under stirring for about 15 hours. After cooling the phases are allowed to separate and the heavy organic phase is separated and washed with 150 g of water. The organic phase is separated again and washed a second time with 150 g of an aqueous HCl solution at 2% by weight. After the organic phase separation the solvent is distilled and the product stripped at 150° C. at a residual pressure of $10^{-2}$ mbar for about 4 hours. 158 g of product are thus obtained with a yield equal to 96%. The IR and NMR ($^{31}P$, $^1H$, $^{13}C$ and $^{19}F$) analyses confirm the product structure.

Application Tests

The phosphazenes of Examples 1–5 have been added to perfluoropolyether lubricating oils and the so obtained compositions have been evaluated in terms of anti-wear properties, as well those of the non additived perfluoropolyether oils and those of the same additived oils according to U.S. Pat. No. 5,124,058. The anti-wear property determination has been carried out by the ASTM D 4172 test.

Three AISI N. E-52100 steel spheres, having a diameter of 12.7 mm, 25 EP (Extra Polish) degree, previously cleaned by washing by immersion in n-hexane (15 min) and subsequently in Galden® HT55 (15') cavity by drying, are put in a vessel having a suitable cavity so as to have three points in contact and, then, they are covered with the lubricant to be tested. A fourth sphere of the same kind, connected to an electric engine which allows its rotation, is placed on the three mentioned soheres with a load of 40±0.2 kgf (392N). The whole is assembled, closed and heated to 75°±2° C. When said temperature has been reached, the fourth sphere, placed over the three of reference, is let rotate at the rate of 1200±60 rpm for 60±1 minutes. At the end of the test the vessel is disassembled, the lubricant is removed and the wear of the three spheres contained therein is evaluated by optical microscopy having a precision of 0.01 mm. The wear value expressed in mm, is obtained as arithmetic mean of six readings, measuring for each sphere, without removing it from the cavity, the wear diameter in the rotation direction and the diameter perpendicular to the first diameter.

For the tests perfluoropolyether lubricating oils having different viscosities have been used, having structure $CF_3O(C_3F_6O)_n(CF_2O)_mCF_3$ wherein n/m=20, commercially known as Fomblin® Y.

Example 6

A mixture formed by 95% by weight of Fomblin® YR1800, having kinematic viscosity measured at 20° C. of 1850 cSt, and 5% by weight of a structure (IIA) compound (Example 3), has been subjected to the ASTM D 4172 test according to the conditions described in the invention. The wear value obtained as an average of six readings is 0.59 mm.

Example 7

The non additived Fomblin® YR1800 is subjected to the ASTM D 4172 test according to the conditions described in the invention. The wear value obtained as an average of six readings is 1.5 mm.

Example 8

A mixture formed by 99% by weight of Fomblin® YR, having a kinematic viscosity measured at 20° C. of 1200 cSt, and 1% by weight of a structure (IIIA) compound (Example 5), has been subjected to the ASTM D 4172 test according to the conditions described in the invention. The wear value obtained as an average of six readings is 0.57 mm.

Example 9

Fomblin® YR, having kinematic viscosity measured at 20° C. of 1,200 cSt, has been subjected to the ASTM D 4172 test according to the conditions described in the invention. The wear value obtained as an average of six readings is 1.3 mm.

Example 10

A mixture formed by 97% by weight of Fomblin® Y45, having a kinematic viscosity measured at 20° C. of 450 cSt, and 3% by weight of a structure (IIIA) compound (Example 5), has been subjected to the ASTM D 4172 test according to the conditions described in the invention. The wear value obtained as an average of six readings is 0.40 mm.

Example 11

Fomblin® Y45, having a kinematic viscosity measured at 20° C. of 450 cSt, has been subjected to the ASTM D 4172 test according to the conditions described in the invention. The wear value obtained as an average of six readings is 1.0 mm.

Example 12

A mixture formed by 99.5% by weight of Fomblin® Y25, having a kinematic viscosity measured at 20° C. of 250 cSt, and 0.5% by weight of a structure (IIIA) compound (Example 5), has been subjected to the ASTM D 4172 test according to the conditions described in the invention. The wear value obtained as an average of six readings is 0.38 mm.

Example 13

A mixture formed by 99.5% by weight of Fomblin® Y25, having a kinematic viscosity measured at 20° C. of 250 cSt, and 0.5% by weight of a structure (IIA) compound (Example 1), has been subjected to the ASTM D 4172 test according to the conditions described in the invention. The wear value obtained as an average of six readings is 0.46 mm.

Example 14

A mixture formed by 99.5% by weight of Fomblin® Y25, having a kinematic viscosity measured at 20° C. of 250 cSt, and 0.5% by weight of a structure (IIA) compound (Example 2), has been subjected to the ASTM D 4172 test according to the conditions described in the invention. The wear value obtained as an average of six readings is 0.47 mm.

Example 15

Fomblin® Y25, having a kinematic viscosity measured at 20° C. of 250 cSt, has been subjected to the ASTM D 4172 test according to the conditions described in the invention. The wear value obtained as an average of six readings is 0.83 mm.

Example 16

A mixture formed by 99.5% by weight of Fomblin® Y25, having a kinematic viscosity measured at 20° C. of 250 cSt, and 0.5% by weight of a structure (IIIA) compound (Example 4), has been subjected to the ASTM D 4172 test according to the conditions described in the invention. The wear value obtained as an average of six readings is 0.40 mm.

Example 17 (Comparative)

Example 6 has been repeated but by using as additive 5% by weight of an additive reported in U.S. Pat. No. 5,124,058 (Example 1) having the following structure:

$$CF_3O—(CF_2O)_n(CF_2CF(CF_3)O)_s(CF(CF_3)O)_p-T$$

wherein $T=CF_2—C(OH)_2CF_3$ (75%)
$CF_2—COOH$ (25%)
s/p=10; s/m=20; p/n=2, said additive indicated in Table 1 as DA 305.

The wear value obtained as an average of six readings is 0.76 mm.

Example 18 (Comparative)

Example 8 has been repeated but by using as additive 1% of the additive described in the Example 17 (comparative). The wear value obtained as an average of six readings is 0.75 mm.

Example 19 (Comparative)

Example 10 has been repeated but by using as additive 3% of the additive described in the Example 17 (comparative). The wear value obtained as an average of six readings is 0.56 mm.

Example 20 (Comparative)

Example 12 has been repeated but by using as additive 1% of the additive described in the Example 17 (comparative). The wear value obtained as an average of six readings is 0.80 mm.

TABLE 1

| | Lubricant viscosity cSt at 20° C. | Additive type | % by weight of additive | Wear, mm |
|---|---|---|---|---|
| 6 | 1850 | IIA (Ex.3) | 5 | 0.59 |
| 7 | 1850 | — | — | 1.50 |
| 8 | 1200 | IIIA (Ex.5) | 1 | 0.57 |
| 9 | 1200 | — | — | 1.30 |
| 10 | 450 | IIIA (Ex.5) | 3 | 0.40 |
| 11 | 450 | — | — | 1.00 |
| 12 | 250 | IIIA (Ex.5) | 0.5 | 0.38 |
| 13 | 250 | IIA (Ex.1) | 0.5 | 0.46 |
| 14 | 250 | IIA (Ex.2) | 0.5 | 0.47 |
| 15 | 250 | — | — | 0.83 |
| 16 | 250 | IIIA (Ex.4) | 0.5 | 0.40 |
| 17 (comp) | 1850 | DA 305 | 5 | 0.76 |
| 18 (comp) | 1200 | DA 305 | 1 | 0.75 |
| 19 (comp) | 450 | DA 305 | 3 | 0.56 |
| 20 (comp) | 250 | DA 305 | 1 | 0.80 |

What is claimed is:

1. Cyclic phosphazene compounds of general formula (I):

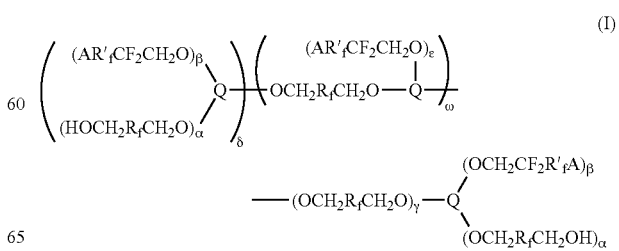

wherein:

Q is a cyclic phazphazene structure

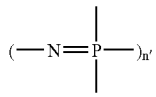

wherein n' is an integer equal to 3 or 4, ω=0 or 1, ε=4 or 6, γ=0 or 1, α and β are integers from 0 to 8, δ=0 or 1, with the proviso that:

when n'=3 and γ=1 then ε=4, α and β are integers from 0 to 5, such that (α+β) is equal to 5; δ=1;

when n'=3 and γ=1 then ε=4, α and β are integers from 0 to 6, such that (α+β) is equal to 6, ω and δ are equal to 0;

when n'=4 and γ=1 then ε is equal to 6, α and β are integers from 0 to 7, such that (α+β) must be equal to 7 and δ=1;

when n'=4 and γ=0 then ε is equal to 6, α and β are integers from 0 to 8, such that (α+β) must be equal to 8, ω and δ are equal to 0;

A is an end group of the —OCF$_2$X, —OC$_2$F$_4$X, —OC$_3$F$_6$X type, wherein X=F, Cl, H; R$_f$ and R'$_f$ are (per)fluoropolyoxyalkylene chains having a number average molecular weight in the range 280–5,000, and comprising one or more repeating units statistically distributed along the chain selected from (C$_3$F$_6$O); (CFYO) wherein Y is F or CF$_3$; (C$_2$F$_4$O); (CF$_2$(CF$_2$)$_{x'}$CF$_2$O) wherein x' is an integer equal to 1 or 2; (CR$_4$R$_5$CF$_2$O) wherein R$_4$ and R$_5$ are equal to or different the one from the other and selected between H, Cl and wherein one fluorine atom of the perfluoromethylene unit can optionally be substituted with H, Cl or (per)fluoroalkyl, preferably having from 1 to 4 carbon atoms, provided that when n'=3, γ=0, α=0, then the phosphazene compounds have general formula (IIA):

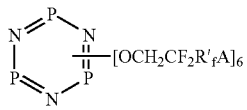

wherein R'$_f$ has structure (a')-(C$_3$F$_6$O)$_q$(CFYO)$_r$—, wherein q and r are integers and q/r≧2 and a number average molecular weight between 500 and 700, Y=—CF$_3$ and A=—OC$_3$F$_6$Cl.

2. Cyclic phosphazene compounds according to claim 1, having formula (III):

wherein:

n' is an integer equal to 3 or 4;

A is an end group of the —OCF$_2$X, —OC$_2$F$_4$X, —OC$_3$F$_6$X type, wherein X=F, Cl, H; ω is an integer equal to 0 or 1;

α and β are integers comprised between 0 and 5, such that α+β must be equal to 5; R$_f$ and R'$_f$ are as above.

3. Cyclic phosphazene compounds according to claim 1, wherein the R$_f$ are selected from the following perfluoropolyoxyalkylene units statistically distributed along the chain:

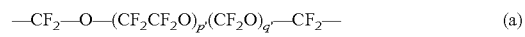  (a)

wherein:

p' and q' are numbers such that the q'/p' ratio is comprised between 0.2 and 2 and the number average molecular weight is in the above range;

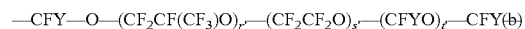  (b)

wherein:

Y is as above; r', s' and t' are numbers such that r'+s' is between 1 and 50, the t'/(r'+s') ratio is comprised between 0.01 and 0.05, and the molecular weight is in the above range;

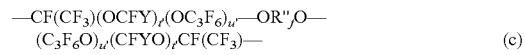  (c)

wherein:

R"$_f$ is a C$_1$–C$_8$ perfluoroalkylene; u'+t' is a number such that the number average molecular weight is in the above range; t' can also have the value of zero; Y is as above;

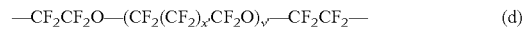  (d)

wherein:

v' is a number such that the molecular weight is in the above range and x' is 1 or 2;

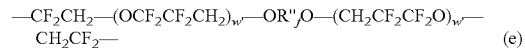  (e)

wherein:

R"$_f$ is as above; w' is a number such that the number average molecular weight is in the above range.

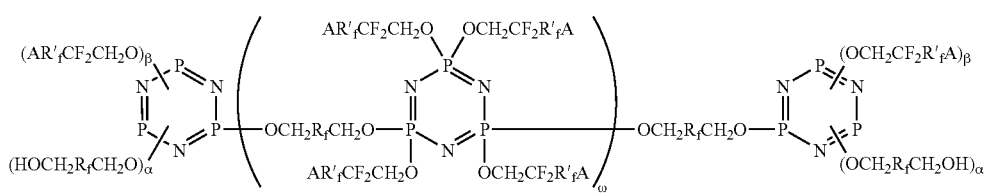

(III)

4. Phosphazene compounds according to claim 1, of general formula (IIB):

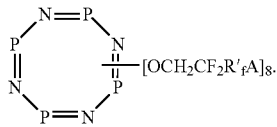 (IIB)

5. Phosphazene compounds according to claim 1, of general formula (IIIA):

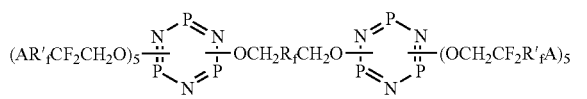 (IIIA)

wherein $R'_f$ has structure (a') and number average molecular weight comprised between 500 and 700, $Y=-CF_3$ and $A=-OC_3F_6Cl$; $R_f$ has structure (a) and a number average molecular weight in the range 1,000–2,000.

6. A method of imparting anti-wear properties to perfluorinated greases and oils comprising the addition to said grease and oils of the cyclic phosphazene compounds of general formula (I):

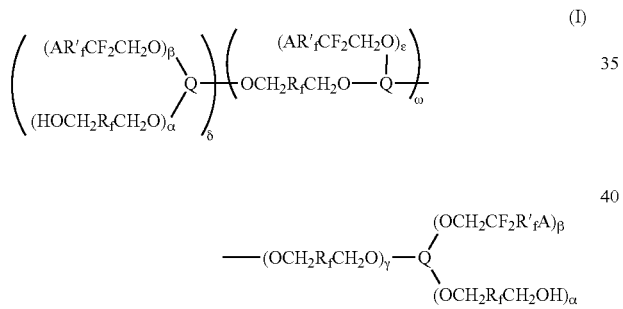 (I)

wherein:

Q is a cyclic phosphazene structure

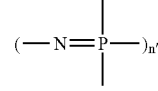

wherein n' is an integer equal to 3 or 4, $\omega=0$ or 1, $\epsilon=4$ or 6, $\gamma=0$ or 1, $\alpha$ and $\beta$ are integers from 0 to 8, $\delta=0$ or 1, with the proviso that:

when n'=3 and $\gamma=1$ then $\epsilon=4$, $\alpha$ and $\beta$ are integers from 0 to 5, such that ($\alpha+\beta$) is equal to 5; $\delta=1$;

when n'=3 and $\gamma=1$ then $\epsilon=4$, $\alpha$ and $\beta$ are integers from 0 to 6, such that ($\alpha+\beta$) is equal to 6, $\omega$ and $\delta$ are equal to 0;

when n'=4 and $\gamma=1$ then $\epsilon$ is equal to 6, $\alpha$ and $\beta$ are integers from 0 to 7, such that ($\alpha+\beta$) must be equal to 7 and $\delta=1$;

when n'=4 and $\gamma=0$ then $\epsilon$ is equal to 6, $\alpha$ and $\beta$ are integers from 0 to 8, such that ($\alpha+\beta$) must be equal to 8, $\omega$ and $\delta$ are equal to 0;

A is an end group of the $-OCF_2X$, $-OC_2F_4X$, $-OC_3F_6X$ type, wherein X=F, Cl, H; $R_f$ and $R'_f$ are (per)fluoropolyoxyalkylene chains having a number average molecular weight in the range 280–5,000 and comprising one or more repeating units statistically distributed along the chain selected from $(C_3F_6O)$; (CFYO) wherein Y is F or $CF_3$; $(C_2F_4O)$; $(CF_2(CF_2)_{x'}CF_2O)$ wherein x' is an integer equal to 1 or 2; $(CR_4R_5CF_2O)$ wherein $R_4$ and $R_5$ are equal to or different the one from the other and selected between H, Cl and wherein one fluorine atom of the perfluoromethylene unit can optionally be substituted with H, Cl or (per)fluoroalkyl having from 1 to 4 carbon atoms.

7. An anti-wear additive of perfluorinated greases and oils comprising the phosphazene compound of claim 1.

8. A method according to claim 6 wherein said cyclic phosphazene compounds have formula (II) or (III):

 (II)

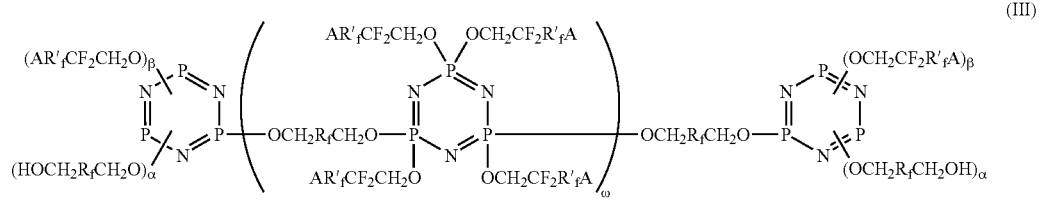 (III)

wherein:

n' is an integer equal to 3 or 4;

A is an end group of the —OCF$_2$X, —OC$_2$F$_4$X, —OC$_3$F$_6$X type, wherein X=F, Cl, H; ω is an integer equal to 0 or 1;

α and β are integers comprised between 0 and 5, such that α+β must be equal to 5; R$_f$ and R'$_f$ are as above.

9. A method according to claim 6 wherein the R$_f$ are selected from the following perfluoropolyoxyalkylene units statistically distributed along the chain:

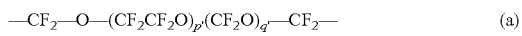   (a)

wherein:

p' and q' are numbers such that the q'/p' ratio is comprised between 0.2 and 2 and the number average molecular weight is in the above range;

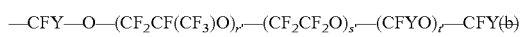   (b)

wherein:

Y is as above; r', s' and t' are numbers such that r'+s' is between 1 and 50, the t'/(r'+s') ratio is comprised between 0.01 and 0.05, and the molecular weight is in the above range;

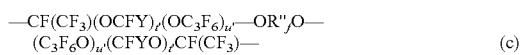   (c)

wherein:

R''$_f$ is a C$_1$–C$_8$ perfluoroalkylene u'+t' is a number such that the number average molecular weight is in the above range; t' can also have the value of zero; Y is as above;

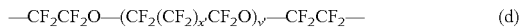   (d)

wherein v' is a number such that the molecular weight is in the above range and x' is 1 or 2;

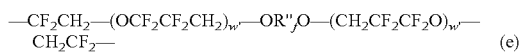   (e)

wherein:

R''$_f$ is as above; w' is a number such that the number average molecular weight is in the above range.

10. A method according to claim 6 wherein the R$_f$ are selected from the following perfluoropolyoxyalkylene units statistically distributed along the chain:

   (a')

wherein Y is —F, —CF$_3$; q and r are integers, the q/r ratio is ≧2;

   (b')

wherein q is an integer, wherein the number average molecular weight is that above mentioned;

   (c')

wherein Y is —F, —CF$_3$; q, t and r are integers such that the number average molecular weight is that above mentioned.

11. A method according to claim 6 wherein the phosphazene compounds have general formula (IIA):

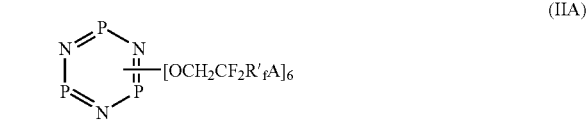   (IIA)

wherein R'$_f$ has structure (a') and a number average molecular weight between 500 and 700, Y=—CF$_3$ and A=—OC$_3$F$_6$Cl.

12. A method according to claim 6 wherein the phosphazene compounds have general formula (IIB):

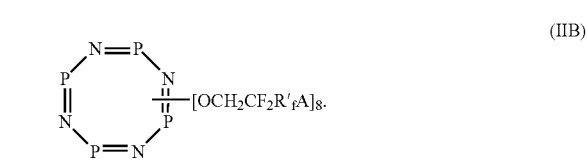   (IIB)

13. A method according to claim 6 wherein the phosphazene compounds have general formula (IIIA):

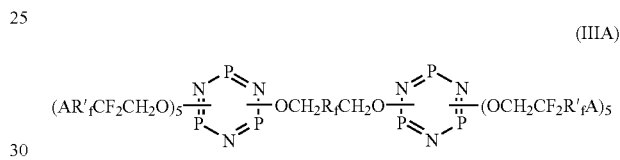   (IIIA)

wherein R'$_f$ has structure (a') and number average molecular weight comprised between 500 and 700, Y=—CF$_3$ and A=—OC$_3$F$_6$Cl; R$_f$ has structure (a) and a number average molecular weight in the range 1,000–2,000.

14. Compositions having lubricating anti-wear properties comprising:

an oil or a grease having a perfluoropolyether structure;
from 0.05 to 10% by weight, of a phosphazene compound of formula (I) or (II) or (III) or (IIA), or (IIB) or (IIIA), of claim 6 or mixtures thereof.

15. Compositions according to claim 14, wherein the perfluoropolyether of the lubricating oil or grease is selected from the following classes:

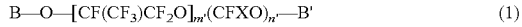   (1)

wherein X is equal to —F or —CF$_3$;

B and B', equal to or different from each other, are selected from —CF$_3$, —C$_2$F$_5$ or —C$_3$F$_7$;

m' and n' are integers such that the m'/n' ratio is in the range 20–1,000 and the product viscosity is in the range 10–4,000 cSt; the various units are statistically distributed along the chain;

   (2)

wherein:

D is equal to —C$_2$F, or —C$_3$F$_7$;

o' is an integer such that the product viscosity is in the above range;

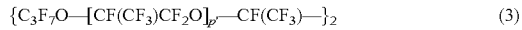   (3)

wherein:

p' is an integer such that the product viscosity is in the above range;

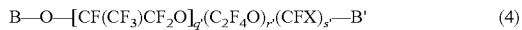   (4)

wherein:

X is equal to —F or —CF$_3$;

B and B', equal to or different from each other, are selected from —CF$_3$, —C$_2$F$_5$ or —C$_3$F$_7$; q', r' and s' are integers, the 0 also comprised, such that the product viscosity is in the above range;

$$B\text{—}O\text{—}(C_2F_4O)_{r'}(CF_2O)_{u'}\text{—}B' \qquad (5)$$

wherein:

B and B', equal to or different from each other, are selected from —CF$_3$, —C$_2$F$_5$ or —C$_3$F$_7$;

t' and u' are integers such that the t'/u' ratio is comprised between 0.1 and 5 and the product viscosity is in the above range;

$$B\text{—}O\text{—}(CF_2CF_2CF_2O)_{v'}\text{—}B' \qquad (6)$$

wherein:

B and B', equal to or different from each other, are selected from —CF$_3$, —C$_2$F$_5$, or —C$_3$F$_7$;

v' is a number such that the product viscosity is in the above range;

$$D\text{-}O\text{—}(CF_2CF_2\text{—}O)_{z'}\text{-}D' \qquad (7)$$

wherein:

D and D', equal to or different from each other, are selected from —C$_2$F$_5$ or —C$_3$F$_7$;

z' is an integer such that the product viscosity is in the above range;

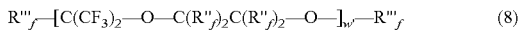
$$R'''_f\text{—}[C(CF_3)_2\text{—}O\text{—}C(R''_f)_2C(R''_f)_2\text{—}O\text{—}]_{w'}\text{—}R'''_f \qquad (8)$$

wherein:

R'''$_f$ is a perfluoroalkyl group;

R''$_f$ is equal to —F or perfluoroalkyl;

w' represents a number higher than or equal to 8.

16. A process to obtain the phosphazene compounds of formula (I), (II) and (III) of claim 6, by reaction, in the presence of a base, of a perchlorophosphazene of formula (IV) or (V):

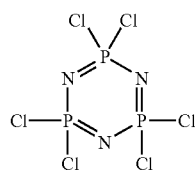

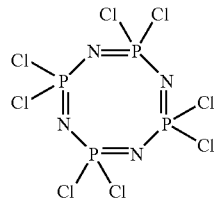

with a fluorinated alcohol of formula AR'$_f$CF$_2$CH$_2$OH or optionally in admixture with an alcohol of formula HOCH$_2$R$_f$CH$_2$OH, wherein A and R$_f$, R'$_f$ have the meaning reported in claim 1, comprising the following steps:

(A) Condensation reaction between a fluorinated alcohol of formula AR'$_f$CF$_2$CH$_2$OH, or a mixture thereof with an alcohol of formula HOCH$_2$R$_f$CH$_2$OH, with the perchloro phosphazene of formula (IV) or (V), in an equivalent ratio alcohol/phosphazenes 1:1, in one or more steps, in an organic solvent, in the presence of a base and of a phase transfer agent, at a temperature in the range 20° C.–100° C., by allowing the phases to separate, at the end of the reaction, and recovering the heavy organic phase, (B) The heavy organic phase obtained in step (A) is repeatedly washed with water and the obtained product is then separated from the solvent.

17. A process according to claim 16, wherein the organic solvent is selected from fluorinated or hydrofluorinated solvents having a boiling point in the range 20° C.–150° C., maintaining a ratio by weight solvent/fluorinated alcohol in the range 0.5–10.

18. A process according to claim 15, wherein it is used as a base an aqueous solution of NaOH or KOH, at a concentration comprised between 20% and 60% w/w, in such amounts to have a KOH or NaOH excess comprised between 2 and 10 times the fluorinated alcohol.

19. A process according to claim 15, wherein the phase transfer agent is a phosphonium salt or a quaternary ammonium salt, used in a molar concentration comprised between 1% and 10% the fluorinated alcohol.

* * * * *